United States Patent
Matsuura et al.

(10) Patent No.: US 10,172,531 B2
(45) Date of Patent: Jan. 8, 2019

(54) HEARTBEAT DETECTION METHOD AND HEARTBEAT DETECTION DEVICE

(71) Applicant: NIPPON TELEGRAPH AND TELEPHONE CORPORATION, Tokyo (JP)

(72) Inventors: Nobuaki Matsuura, Tokyo (JP); Kei Kuwabara, Tokyo (JP); Kazuhiko Takagahara, Tokyo (JP); Ryusuke Kawano, Tokyo (JP); Hiroshi Koizumi, Tokyo (JP)

(73) Assignee: NIPPON TELEGRAPH AND TELEPHONE CORPORATION, Tokyo (JP)

(*) Notice: Subject to any disclaimer, the term of this patent is extended or adjusted under 35 U.S.C. 154(b) by 0 days.

(21) Appl. No.: 15/508,068

(22) PCT Filed: Aug. 28, 2015

(86) PCT No.: PCT/JP2015/074405
§ 371 (c)(1),
(2) Date: Mar. 1, 2017

(87) PCT Pub. No.: WO2016/035701
PCT Pub. Date: Mar. 10, 2016

(65) Prior Publication Data
US 2017/0281021 A1    Oct. 5, 2017

(30) Foreign Application Priority Data
Sep. 4, 2014  (JP) .................................. 2014-179869

(51) Int. Cl.
*A61B 5/0245* (2006.01)
*A61B 5/00* (2006.01)
(Continued)

(52) U.S. Cl.
CPC ........ *A61B 5/0245* (2013.01); *A61B 5/02405* (2013.01); *A61B 5/0456* (2013.01);
(Continued)

(58) Field of Classification Search
CPC ... A61B 5/0245; A61B 5/0456; A61B 5/7278; A61B 5/7207
See application file for complete search history.

(56) References Cited

U.S. PATENT DOCUMENTS

2009/0156948 A1    6/2009   Shimizu et al.

FOREIGN PATENT DOCUMENTS

| CN | 101272731 A | 9/2008 |
| CN | 101933803 A | 5/2011 |

(Continued)

OTHER PUBLICATIONS

"ECG Implementation on the TMS320C5515 DSP Medical Development Kit (MDK) with the ADS1298 ECG-FE", Texas Instruments Incorporated, <http://www.ti.com/lit/an/sprabj1/sprabj1.pdf>, 2011.

*Primary Examiner* — William Levicky
(74) *Attorney, Agent, or Firm* — Womble Bond Dickinson (US) LLP

(57) ABSTRACT

A heartbeat detection device includes a difference value calculation unit (3) for calculating, from a sampling data sequence of an electrocardiographic waveform of a living body, one of an amount of change and a degree of change of sampling data for each sampling time, a multiplication unit (4) for calculating, for each sampling time, a product by multiplying one of an amount of change and a degree of change of the sampling data at a time K by one of the sampling data at the time K and sampling data at a time before the time K by a predetermined time t, a peak detection unit (5) for detecting a peak of the product, and a heartbeat
(Continued)

time determination unit (6) for setting time of the peak of the product as a heartbeat time.

10 Claims, 11 Drawing Sheets

(51) Int. Cl.
    *A61B 5/0456*     (2006.01)
    *A61B 5/024*     (2006.01)
    *A61B 5/117*     (2016.01)

(52) U.S. Cl.
    CPC ............ *A61B 5/117* (2013.01); *A61B 5/7235* (2013.01); *A61B 5/7278* (2013.01)

(56) References Cited

FOREIGN PATENT DOCUMENTS

| | | |
|---|---|---|
| JP | H10-192250 A | 7/1998 |
| JP | H11-197128 A | 7/1999 |
| JP | 2002-078695 A | 3/2002 |
| JP | 2003-000561 A | 1/2003 |
| WO | WO 2004/078258 A1 | 9/2004 |

HEARTBEAT DETECTION METHOD AND HEARTBEAT DETECTION DEVICE

TECHNICAL FIELD

The present invention relates to a heartbeat detection method and heartbeat detection device for extracting biological information such as a heartbeat interval (R-R interval) from an electrocardiographic waveform.

BACKGROUND ART

An ECG (Electrocardiogram) waveform is obtained by observing and recording the electrical activity of a heart, and is measured by attaching electrodes to a body surface in a general method. As an ECG waveform lead system, that is, an electrode arrangement, there are various types using limbs and chest. In the V3 to V5 leads among precordial leads, an electrode is arranged at the left chest. In the CC5 lead suitable for monitoring an ECG waveform for a long time, electrodes are arranged at the symmetrical positions of left and right chests. These leads have the advantage that a stable waveform having a large amplitude is obtained.

FIG. 9 shows an example of an ECG waveform. In FIG. 9, the ordinate represents the electric potential and the abscissa represents the time. The ECG waveform is formed from continuous heartbeat waveforms, and one heartbeat waveform is formed from components such as P, Q, R, S, and T waves reflecting the activities of atriums and ventricles.

It is known that biological information such as an R-R interval obtained from an ECG waveform is an index reflecting the autonomic activity. It is useful for evaluation of the autonomic function to obtain an ECG waveform in daily life and analyze data of a heartbeat fluctuation from detected heartbeats. Furthermore, there is an application in which an exercise tolerance is estimated from heartbeat data during an exercise, and used for optimization or the like.

As a conventional heartbeat detection method, the following literatures are known. Japanese Patent Laid-Open No. 2002-78695 discloses an arrangement for removing the fluctuation of the baseline of an ECG waveform. In addition, Japanese Patent Laid-Open No. 2003-561 discloses an arrangement of recognizing an R wave using a threshold based on an amplitude between the peak and valley of a waveform.

A method of obtaining the R-R interval or the like based on a change in value obtained by calculating the first derivative of an ECG waveform is described in "ECG Implementation on the TMS320C5515 DSP Medical Development Kit (MDK) with the ADS1298 ECG-FE", Texas Instruments Incorporated, <http://www.ti.com/lit/an/sprabjl/sprabjl.pdf>, 2011. In this heartbeat detection method, more specifically, the absolute value of the difference between the (n+1)th sampling value and the (n-1)th sampling value is obtained, peaks are detected based on a threshold, and then the time width between two peaks is set as the R-R interval.

DISCLOSURE OF INVENTION

Problem to be Solved by the Invention

However, the above-described heartbeat detection method has the following problem. That is, if heartbeat data in daily life or during an exercise is to be recorded or analyzed, noise caused by a body motion or the like may be mixed into an ECG waveform, unlike measurement in a rest state.

FIGS. 10 and 11 show graphs for explaining the conventional problem, in which the abscissa represents the time [ms] and the ordinate represents the electric potential [arbitrary unit] replaced by a digital value. In FIGS. 10 and 11, X represents an example of sampling data of an ECG waveform, and R represents an R wave to be detected as a heartbeat. The ECG waveforms in FIGS. 10 and 11 are identical.

In FIGS. 10 and 11, although a normal ECG waveform pattern is observed after 21,000 ms, noise components are superimposed on the original ECG waveform before 21,000 ms. Even if an attempt is made to detect a heartbeat based on a threshold from such ECG waveform, an amplitude fluctuation is large, and it is thus difficult to set an appropriate threshold. Furthermore, even if a threshold is periodically updated in accordance with a peak value, the threshold is increased in a portion including noise. As a result, a heartbeat in a portion without any noise is unnecessarily missed.

On the other hand, there is also provided a method of detecting a heartbeat based on the derivative of an ECG waveform. In general, an ECG waveform is processed as a discrete data sequence in data processing. Therefore, obtaining the derivative of an ECG waveform is equivalent to obtaining the time subtraction of the ECG waveform. In FIG. 10, DF is obtained by plotting, at each time of sampling data X of the ECG waveform, a value obtained by subtracting a value 5 ms before from a value 5 ms after, that is, a first derivative. In a usual ECG waveform, an abrupt change from the R wave to the S wave can be made conspicuous by obtaining the first derivative, thereby facilitating detection of a heartbeat. However, the first derivative values DF in FIG. 10 include noise components which abruptly change. Thus, the noise components may be misidentified as heartbeats, and it is difficult to detect heartbeats based on the first derivative values. In FIG. 10, N represents a noise component which is readily misidentified as a heartbeat.

In FIG. 11, DS is obtained by plotting, at each of times of the first derivative values DF in FIG. 10, a value obtained by subtracting a value 5 ms before from a value 5 ms after, that is, a second derivative. The second derivative values DS in FIG. 11 also include peaks by noise components which are readily misidentified as heartbeats in addition to peaks of heartbeats.

The present invention has been made to solve the above-described problem, and has as its object to provide a heartbeat detection method and heartbeat detection device, which can appropriately detect a heartbeat and its time from data in which noise caused by a body motion is superimposed on an ECG waveform.

Means of Solution to the Problem

According to the present invention, there is provided a heartbeat detection method comprising a calculation step of calculating, from a sampling data sequence of an electrocardiographic waveform of a living body, one of an amount of change and a degree of change of sampling data for each sampling time, a multiplication step of calculating, for each sampling time, a product by multiplying one of an amount of change and a degree of change of the sampling data at a time K by one of the sampling data at the time K and sampling data at a time before the time K by a predetermined time t, a peak detection step of detecting a peak of the product, and a heartbeat time determination step of setting time of the peak of the product as a heartbeat time.

According to the present invention, there is also provided a heartbeat detection device comprising calculation means for calculating, from a sampling data sequence of an electrocardiographic waveform of a living body, one of an amount of change and a degree of change of sampling data for each sampling time, multiplication means for calculating, for each sampling time, a product by multiplying one of an amount of change and a degree of change of the sampling data at a time K by one of the sampling data at the time K and sampling data at a time before the time K by a predetermined time t, peak detection means for detecting a peak of the product, and heartbeat time determination means for setting time of the peak of the product as a heartbeat time.

Effect of the Invention

According to the present invention, the change mount or the degree of change of sampling data is calculated for each sampling time from the sampling data sequence of the electrocardiographic waveform of a living body, a product is calculated for each sampling time by multiplying the amount of change or the degree of change of the sampling data at a time K by sampling data at a time K or sampling data at time a predetermined time t before time K, the peak of the product is detected, and time of the peak of the product is set as a heartbeat time. In the present invention, it is possible to emphasize a peak component derived from a heartbeat, and to correctly detect a heartbeat even from a sampling data sequence in which noise caused by a body motion is superimposed on an electrocardiographic waveform.

BEST MODE FOR CARRYING OUT THE INVENTION

[Principle of Invention]
FIGS. 1 to 4 show graphs for explaining a principle according to the present invention. In FIGS. 1 to 4, the abscissa represents the time [ms] and the ordinate represents the electric potential [arbitrary unit] replaced by a digital value.

Figure 1:
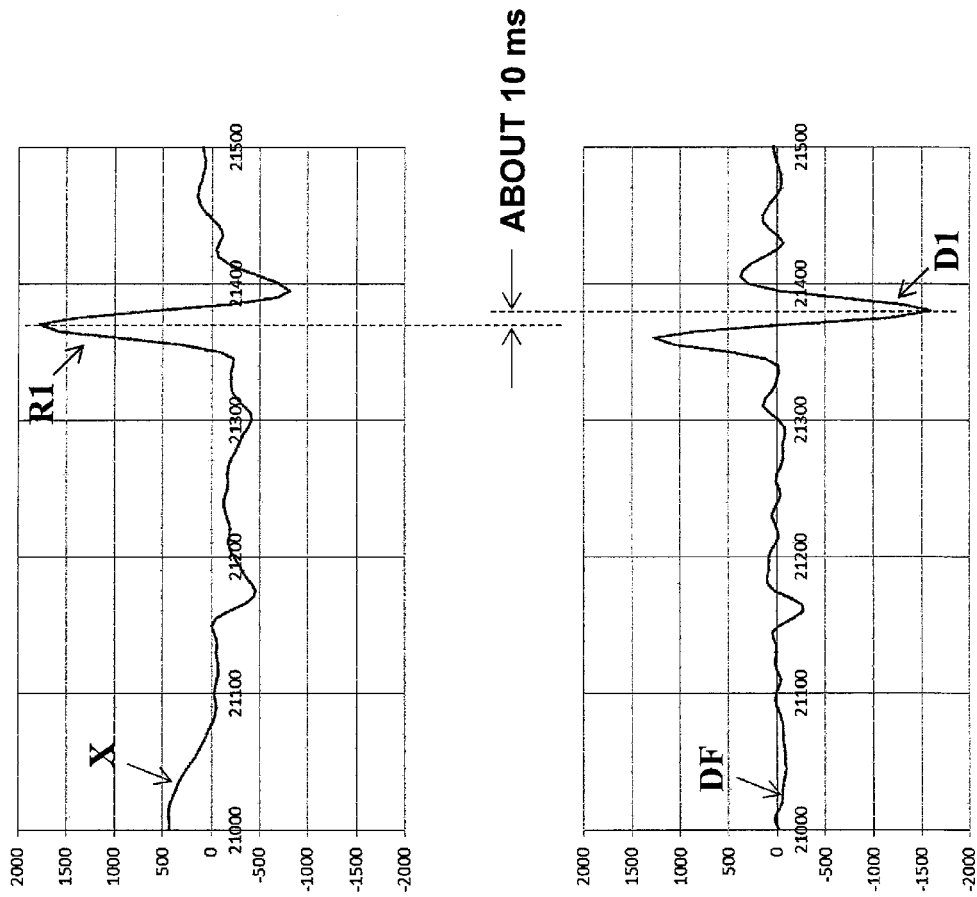
FIG. 1 shows graphs for explaining a principle according to the present invention.
Figure 10:
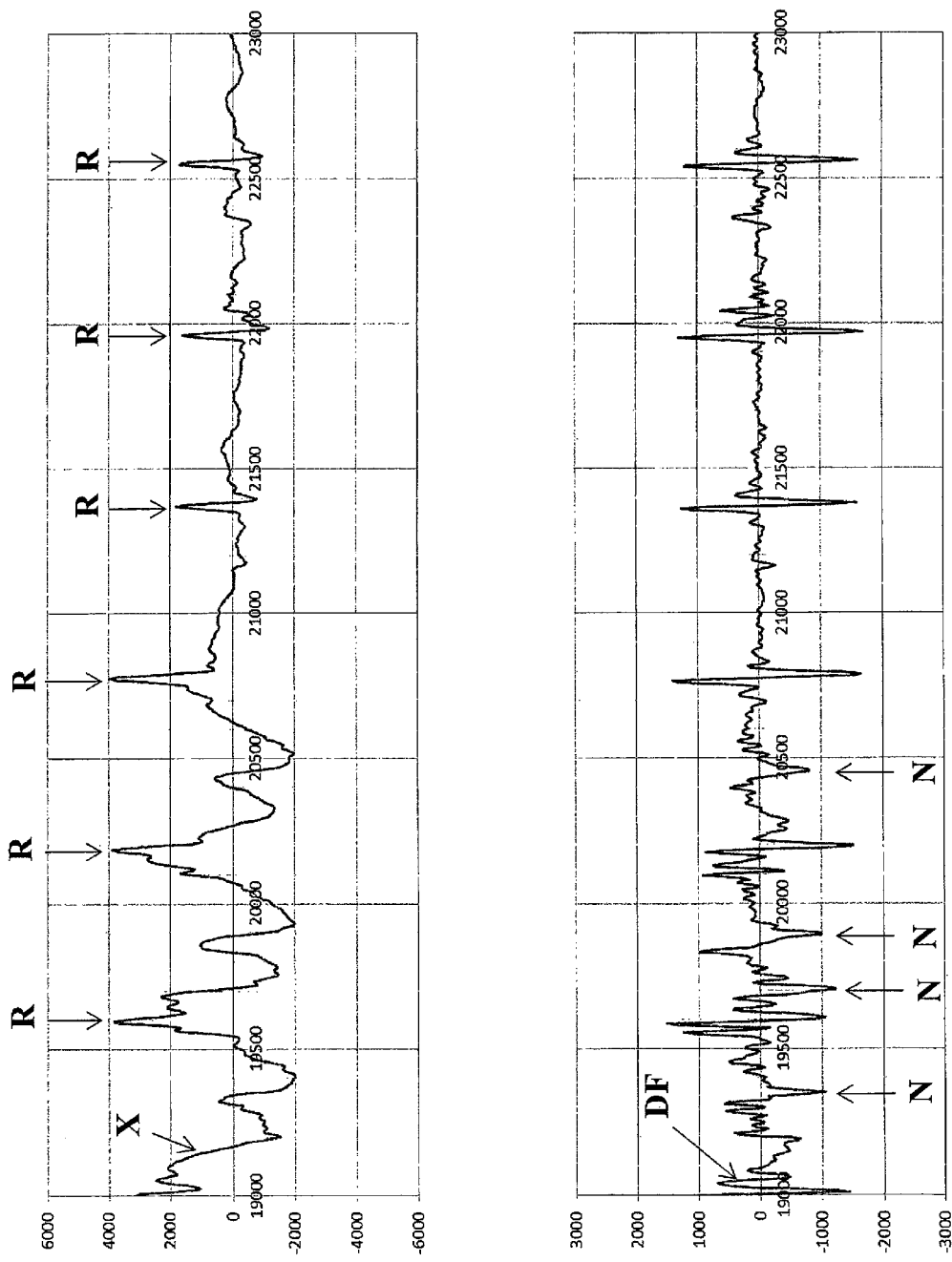
FIG. 10 shows graphs for explaining the conventional problem.

FIG. 1 shows enlarged graphs of portions in FIG. 10. It is understood that a peak R1 of an R wave in FIG. 1 is at time 10 ms before a peak D1 of a first derivative value DF. Therefore, to emphasize the peaks R1 and D1, a data sequence obtained by multiplying the first derivative value DF as the difference value between values before and after a sampling value X by a sampling value 10 ms before the sampling value X is tracked.

Figure 2:
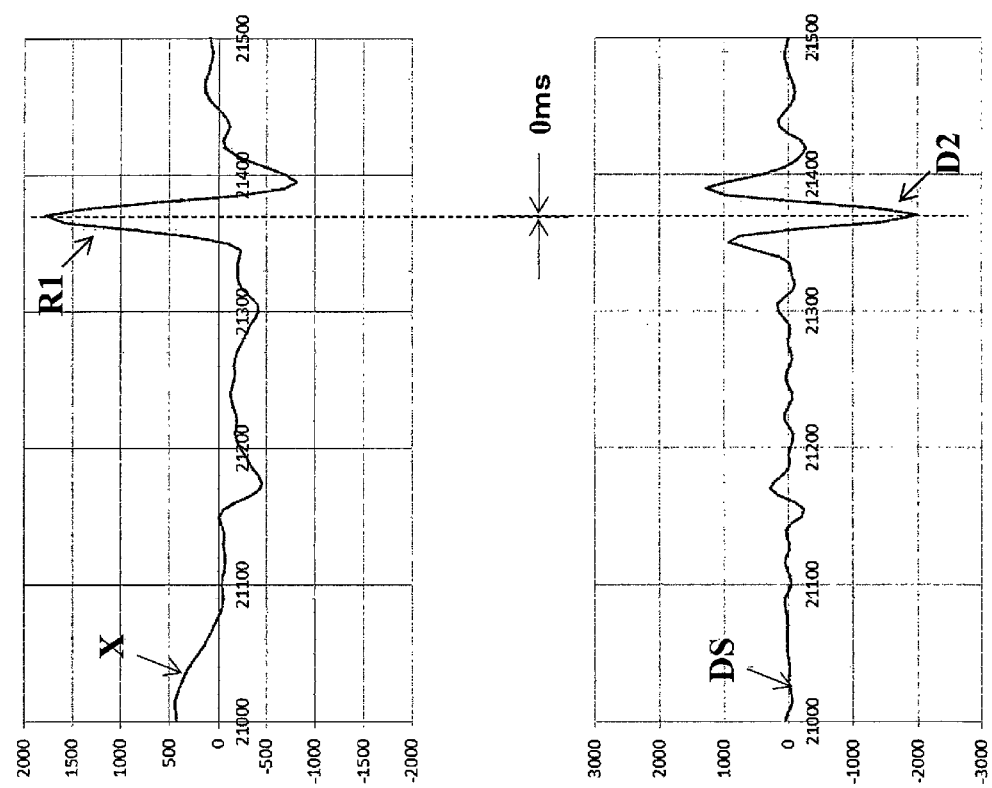
FIG. 2 shows graphs for explaining the principle according to the present invention.
Figure 11:
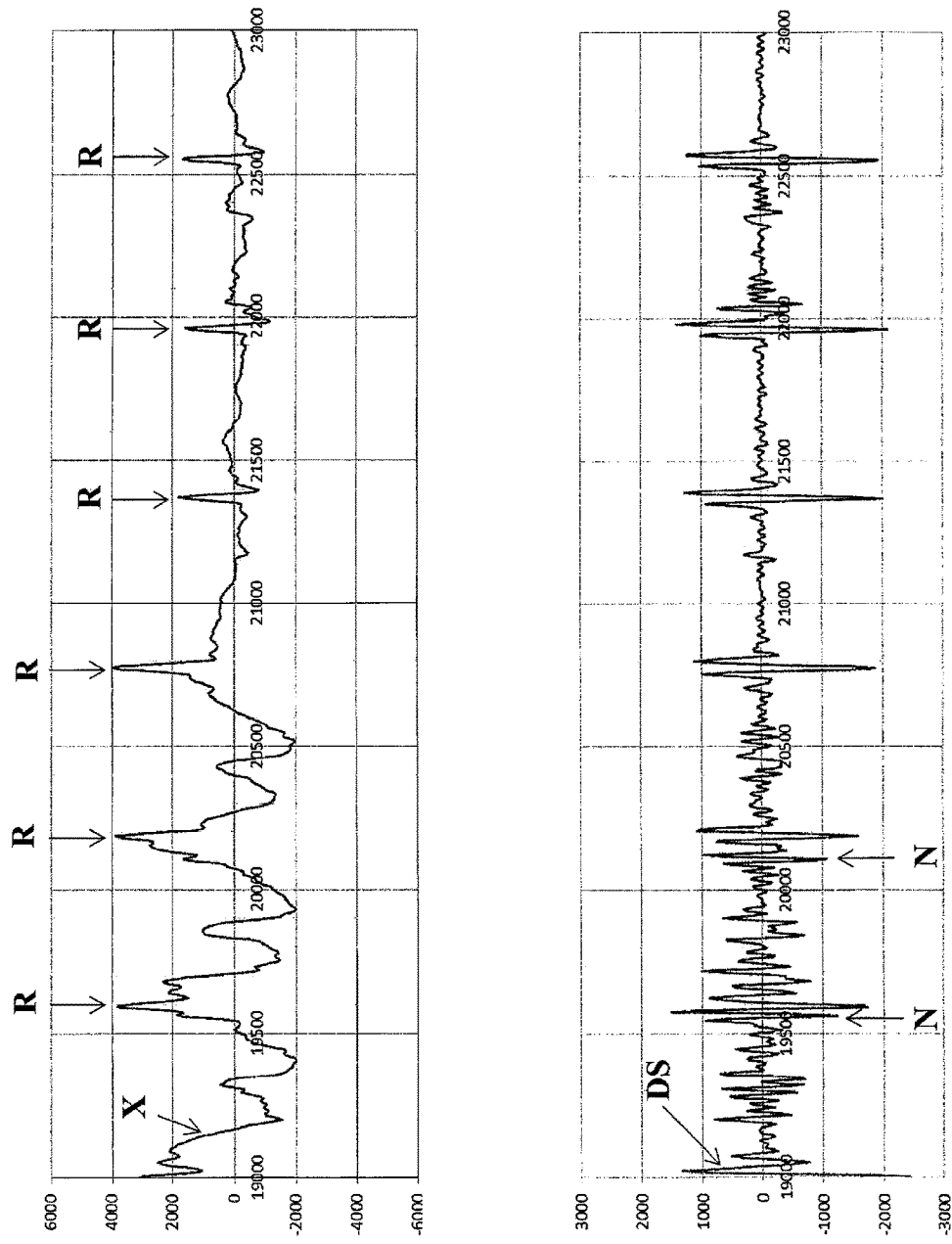
FIG. 11 shows graphs for explaining the conventional problem.

FIG. 2 shows enlarged graphs of portions in FIG. 11. It is understood that the peak R1 of the R wave in FIG. 2 is at the same position as that of a peak D2 of a second derivative value DS.

Figure 3:
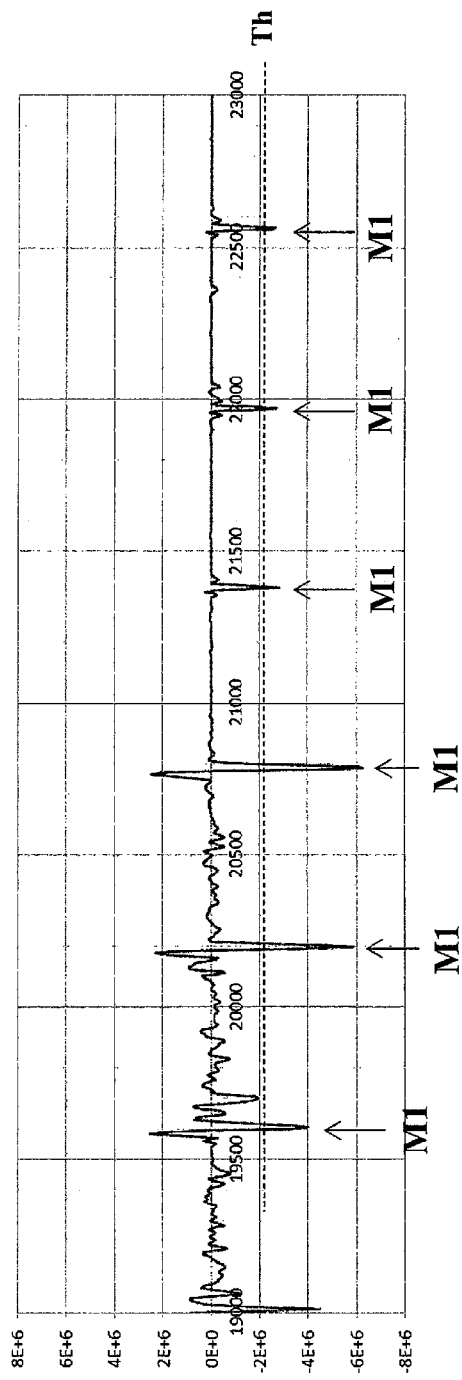
FIG. 3 is a graph for explaining the principle according to the present invention.

FIG. 3 is a graph obtained by plotting a value calculated by multiplying the first derivative value DF at each time in FIG. 10 by the sampling value X 10 ms before the time. It will be apparent from FIG. 3 that while peaks M1 corresponding to heartbeats are emphasized, noise components between heartbeats shown in FIG. 10 are reduced, and the peaks M1 corresponding to the heartbeats can be detected based on a threshold Th.

Figure 4:
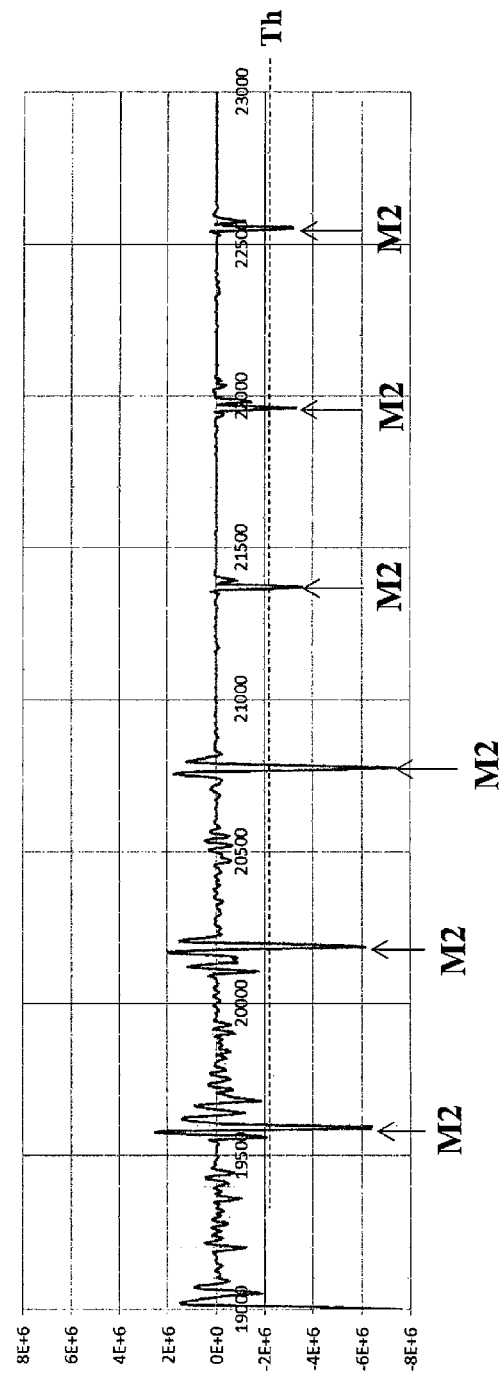
FIG. 4 is a graph for explaining the principle according to the present invention.

Similarly, FIG. 4 is a graph obtained by plotting a value calculated by multiplying the second derivative value DS at each time in FIG. 11 by the sampling value X at the time in FIG. 11. It will be apparent from FIG. 4 that noise components are reduced, similarly to FIG. 3, and peaks M2 corresponding to heartbeats can be detected based on the threshold Th.

As described above, according to the present invention, in the sampling data sequence of the ECG waveform, the amount of change or the degree of change of the sampling value at given time is multiplied by the sampling value at the given time or a sampling value at time a predetermined time t before the given time, thereby setting time of the peak of the product as a heartbeat time.

The sampling data sequence of the ECG waveform includes a peak component corresponding to an R wave for each heartbeat. Furthermore, a data sequence obtained by calculating the derivative of the ECG waveform includes, for each heartbeat, a peak component corresponding to an abrupt change between an R wave and an S wave. That is, each of the data sequences includes peak components of the same beating rhythm. If these data sequences are overlaid by shifting them by a given time width, the peak components are synchronized with each other. Therefore, by multiplying the data sequences under appropriate conditions, it is possible to emphasize the peak components derived from the heartbeats. On the other hand, the fluctuation components of noise caused by a body motion or the like appear regardless of the heartbeats, and tend to be smoothed by multiplying the data sequences. As a result, it is possible to make only the heartbeats conspicuous, thereby facilitating detection of them.

As a value for observing a change in ECG waveform along with an abrupt change between the R wave and the S wave, the first derivative or the second derivative presenting a unimodal waveform is appropriately used. In the sampling data sequence of the ECG waveform, the first derivative value of a sampling value at a time K is obtained by subtracting a sampling value at time (K−W) from a sampling value at time (k+W) (W is, for example, 5 ms). If the amount of change of the sampling value at a time K, that is, the first derivative value is used as a value by which the sampling value is multiplied, a sampling value at time (K−t) the predetermined time t before time K is multiplied by the first derivative value. The peak of the first derivative value appears about 10 to 12 ms after the peak of the R wave of the ECG waveform. Therefore, if the first derivative value is used, the predetermined time t is set to satisfy 10 ms≤t≤12 ms.

The second derivative value of the sampling value at a time K is obtained by subtracting the first derivative value of the sampling value at time (k−W) from the first derivative value of the sampling value at time (K+W). If the degree of change of the sampling value at a time K, that is, the second derivative value is used as a value by which the sampling value is multiplied, the sampling value at a time K or the sampling value at time (K−t) the predetermined time t before time K is multiplied by the second derivative value. The peak of the second derivative value appears about 0 to 1 ms after the peak of the R wave of the ECG waveform. Therefore, if the second derivative value is used, the predetermined time t is set to satisfy 0 ms<t≤1 ms.

The R and S waves of the ECG waveform are obtained by capturing a current along with a change in potential when the depolarization of the ventricular muscle cells progresses from endocardium to epicardium, and the movement and speed of the current are hardly influenced by an individual difference such as a body type difference. Therefore, the time interval between the peaks is almost constant.

Embodiment

Figure 5:
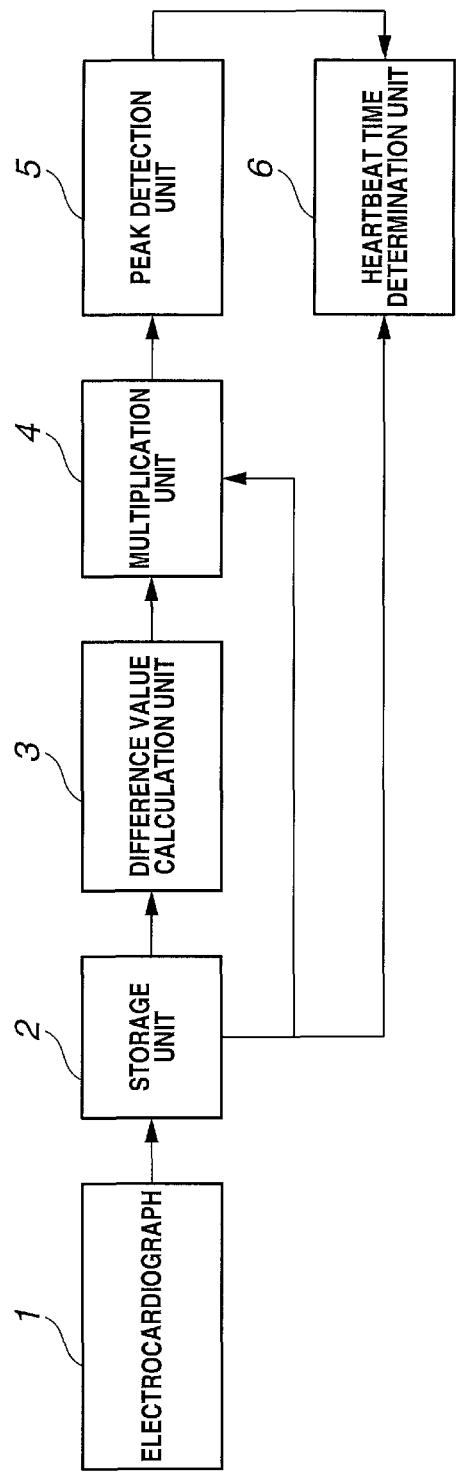
FIG. 5 is a block diagram showing the arrangement of a heartbeat detection device according an embodiment of the present invention.

An embodiment of the present invention will be described below with reference to the accompanying drawings. FIG. 5 is a block diagram showing the arrangement of a heartbeat detection device according to the embodiment of the present invention. The heartbeat detection device includes an electrocardiograph 1, a storage unit 2, a difference value calculation unit 3 (calculation means), a multiplication unit 4 (multiplication means), a peak detection unit 5 (peak detection means), and a heartbeat time determination unit 6 (a heartbeat time determination means).

A heartbeat detection method according to the embodiment will be described below. In this specification, a procedure of detecting a heartbeat and calculating a heartbeat time of the heartbeat will be explained. By repeating calculation of a heartbeat time for the period of ECG waveform data, sequential data of heartbeat times are successively obtained, and the index of a heartbeat fluctuation can be calculated from the sequential data.

In this embodiment, X(i) represents a data sequence obtained by sampling the ECG waveform where i (i=1, 2, . . . ) represents a number assigned to one sampling data. As the number i is larger, sampling time is later, as a matter of course. Furthermore, a represents an integer obtained by dividing, by the sampling interval, half (W described above) the time interval when obtaining the first derivative value of the sampling data X(i), b represents an integer obtained by dividing, by the sampling interval, a constant time difference t provided when multiplying the sampling data X(i) by its first derivative value, and Th represents the threshold for obtaining the peak of the product of the sampling data X(i) and its first derivative value.

The electrocardiograph 1 measures the ECG waveform of a living body (human body) (not shown), and outputs the sampling data sequence X(i) of the ECG waveform. At this time, the electrocardiograph 1 outputs the data sequence by adding sampling time information to each sampling data. Note that a practical method of measuring the ECG waveform is a well-known technique and a detailed description thereof will be omitted.

The storage unit 2 stores the sampling data sequence X(i) of the ECG waveform and the sampling time information, which have been output from the electrocardiograph 1.

Figure 6:
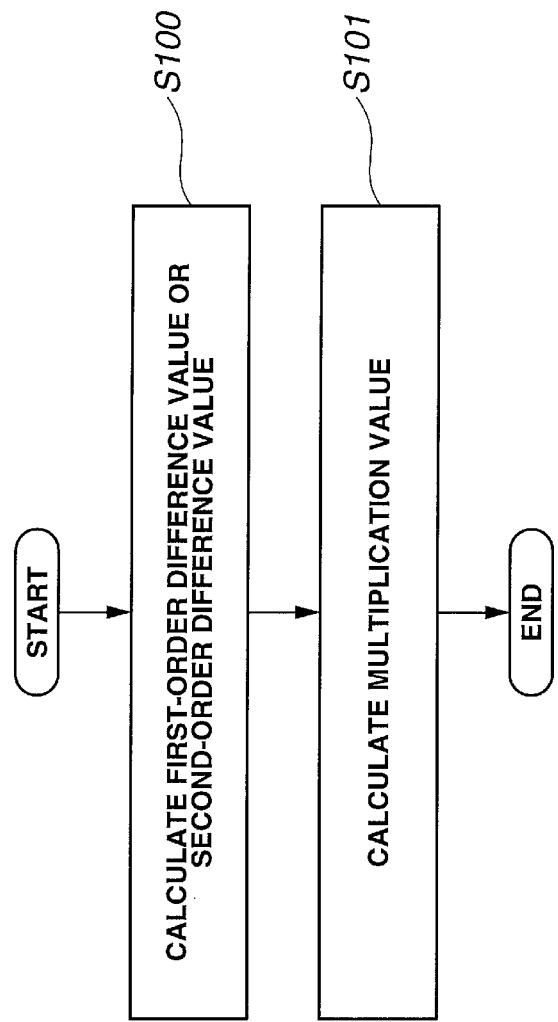
FIG. 6 is a flowchart for explaining the operations of the difference value calculation unit and multiplication unit of the heartbeat detection device according to the embodiment of the present invention.

FIG. 6 is a flowchart for explaining the operations of the difference value calculation unit 3 and multiplication unit 4. The difference value calculation unit 3 calculates the first derivative value (X(i+a)−X(i−a)) of the sampling data X(i) for each sampling time (step S100 of FIG. 6).

The multiplication unit 4 calculates, for each sampling time, a product (X(i+a)−X(i−a))×X(i−b) of the first derivative value (X(i+a)−X(i−a)) of the sampling data X(i) and sampling data X(i−b) at time the predetermined time t before the sampling data X(i) (step S101 of FIG. 6).

Figure 7:
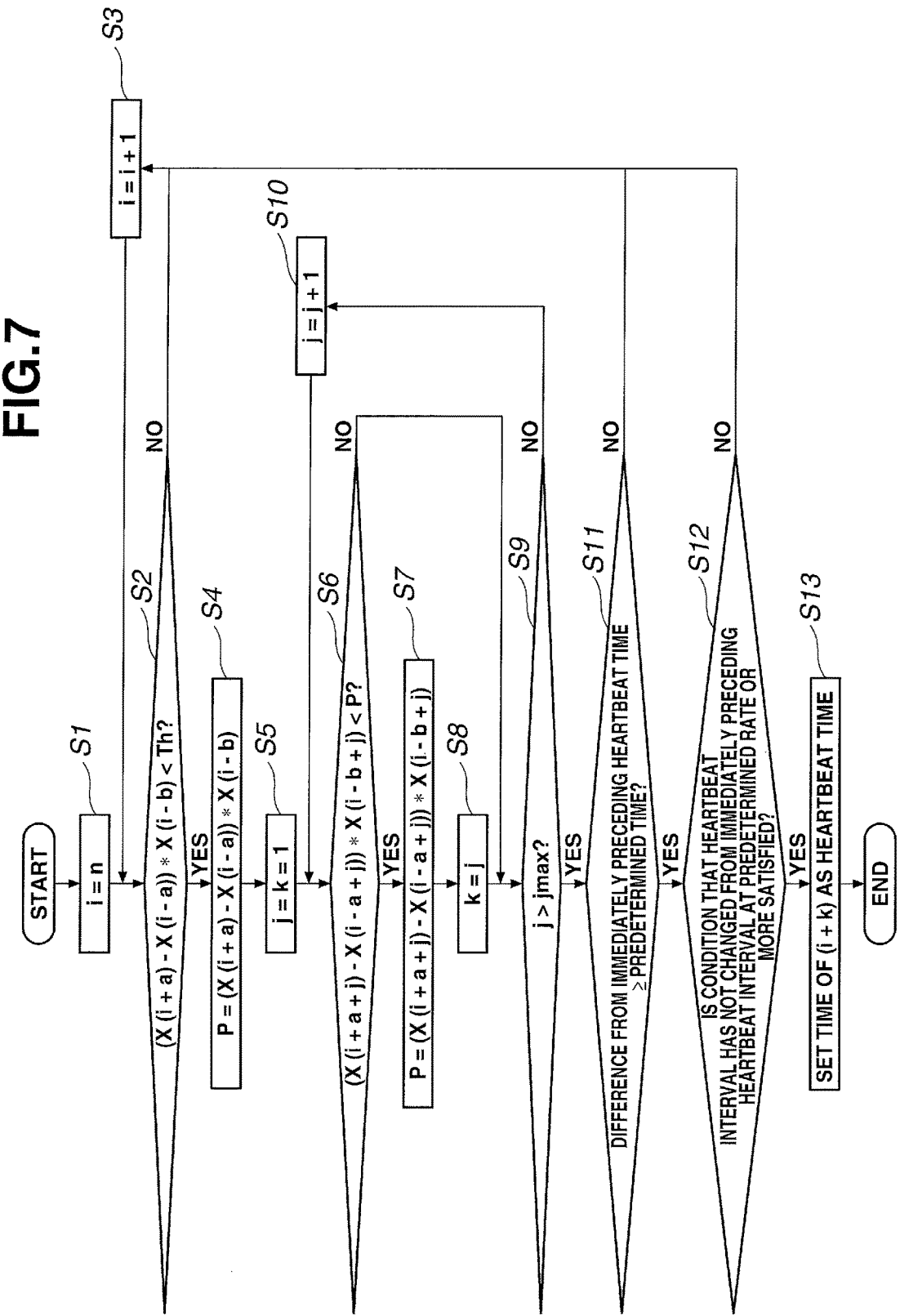
FIG. 7 is a flowchart for explaining the operations of the peak detection unit and heartbeat time determination unit of the heartbeat detection device according to the embodiment of the present invention.

FIG. 7 is a flowchart for explaining the operations of the peak detection unit 5 and heartbeat time determination unit 6. The peak detection unit 5 searches for a point at which the product (X(i+a)−X(i−a))×X(i−b) exceeds the threshold Th.

First, the peak detection unit 5 sets the number (counter variable) i for successively reading out the sampling data sequence X(i) to an initial value (n in this example) (step S1 of FIG. 7). Next, the peak detection unit 5 compares the product (X(i+a)−X(i−a))×X(i−b) calculated by the multiplication unit 4 with the threshold Th (step S2 of FIG. 7).

If the product (X(i+a)−X(i−a))×X(i−b) is equal to or larger than the threshold Th (NO in step S2), the peak detection unit 5 determines that there is no peak of the product near time indicated by i, sets i=i+1 (step S3 of FIG. 7), and returns to step S2. The processes in steps S2 and S3 are repeated until the product (X(i+a)−X(i−a))×X(i−b) becomes smaller than the threshold Th.

If it is determined in step S2 that the product (X(i+a)−X(i−a))×X(i−b) is smaller than the threshold Th, the peak detection unit 5 determines that there is the peak of the product near time indicated by i, and advances to a procedure of specifying a peak position in step S4 and subsequent steps.

The peak detection unit 5 temporarily sets a peak value P to (X(i+a)−X(i−a))×X(i−b) and stores it (step S4 of FIG. 7). The peak detection unit 5 sets a counter variable j for detecting the peak of the product and a variable k indicating the peak position to 1 (step S5 of FIG. 7).

The peak detection unit 5 compares the product (X(i+a+j)−X(i−a+j))×X(i−b+j) calculated by the multiplication unit 4 with the current peak value P (step S6 of FIG. 7). If the product (X(i+a+j)−X(i−a+j))×X(i−b+j) is equal to or larger than the peak value P (NO in step S6), the process advances to step S9 without changing the peak value P and the value of the variable k.

If the product (X(i+a+j)−X(i−a+j))×X(i−b+j) is smaller than the current peak value P, the peak detection unit 5 updates the peak value P to (X(i+a+j)−X(i−a+j))×X(i−b+j), and stores it (step S7 of FIG. 7). The peak detection unit 5 replaces the variable k by j (step S8 of FIG. 7), and advances to step S9. In step S9, the peak detection unit 5 determines whether the counter variable j does not exceed a predetermined value jmax designating a range within which the peak value is obtained.

If the counter variable j does not exceed the predetermined jmax, the peak detection unit 5 sets j=j+1 (step S10 of FIG. 7), and returns to step S6. The processes in steps S6 to S10 are repeated until the counter variable j exceeds the predetermined value jmax. If the counter variable j exceeds the predetermined value jmax, the peak detection unit 5 ends the search for the peak value P based on the counter variable j. At this time, time of the newest peak value P, that is, time indicated by (i+k) is a candidate of a heartbeat time.

Next, the heartbeat time determination unit 6 determines whether the detected heartbeat time is appropriate, and selectively fixes a heartbeat time.

First, the heartbeat time determination unit 6 determines whether the difference between time T indicated by (i+k) and an immediately precedingly detected heartbeat time $T_{(-1)}$ is equal to or longer than a predetermined time (step S11 of FIG. 7). If the difference between time T and the immediately preceding heartbeat time $T_{(-1)}$ is shorter than the predetermined time, the heartbeat time determination unit 6 discards time T indicated by (i+k) without adopting it as a heartbeat time, and returns to step S3.

A general normal value range exists for the heartbeat interval. If a very short heartbeat interval, as compared with the range, is detected, noise superimposed on an electrocardiographic waveform due to a body motion or the like is erroneously recognized as a heartbeat at high probability. It is possible to prevent erroneous detection caused by noise or the like by setting the condition that the difference between time T of the detected peak of the product and the immediately preceding heartbeat time $T_{(-1)}$ is equal to or longer than the predetermined time.

Furthermore, the heartbeat time determination unit 6 determines whether a heartbeat interval $(T-T_{(-1)})$ when time T indicated by (i+k) is considered as a heartbeat time has not increased from an immediately preceding heartbeat interval $(T_{(-1)}-T_{(-2)})$ at a predetermined rate or more (step S12 of FIG. 7). If the increasing rate $(T-T_{(-1)})/(T_{(-1)}-T_{(-2)})$ of the heartbeat interval is equal to or higher than a predetermined value, the heartbeat time determination unit 6 determines that the heartbeat interval has increased at the predetermined rate or more, and discards time T indicated by (i+k) without adopting it as a heartbeat time, thereby returning to step S3.

If detection of a given heartbeat fails, data obtained as the heartbeat interval between heartbeats before and after the given heartbeat indicates a value about twice larger than an actual value, and is inappropriately used for evaluation of the autonomic function or the like. It is possible to exclude the erroneous data, for which detection of a heartbeat has failed, from the analysis target of the biological information by setting the condition that the detected heartbeat interval has not increased at the predetermined rate or more.

If the difference between time T indicated by (i+k) and the immediately preceding heartbeat time $T_{(-1)}$ is equal to or longer than the predetermined time, and the increasing rate $(T-T_{(-1)})/(T_{(-1)}-T_{(-2)})$ of the heartbeat interval is lower than the predetermined value, the heartbeat time determination unit 6 adopts time T indicated by (i+k) as a heartbeat time (step S13 of FIG. 7).

After the end of step S13, i=i+1 is set and the process returns to step S2. This starts detection of the next heartbeat. Alternatively, the values of i, the number of which corresponds to a predetermined time shorter than the minimum value of the heartbeat interval to be detected, may be skipped, and the process may returns to step S2. By repeating the processes in steps S2 to S13, it is possible to obtain the sequential data of the heartbeat times, and obtain the index of a heartbeat fluctuation from the sequential data.

Figure 8:
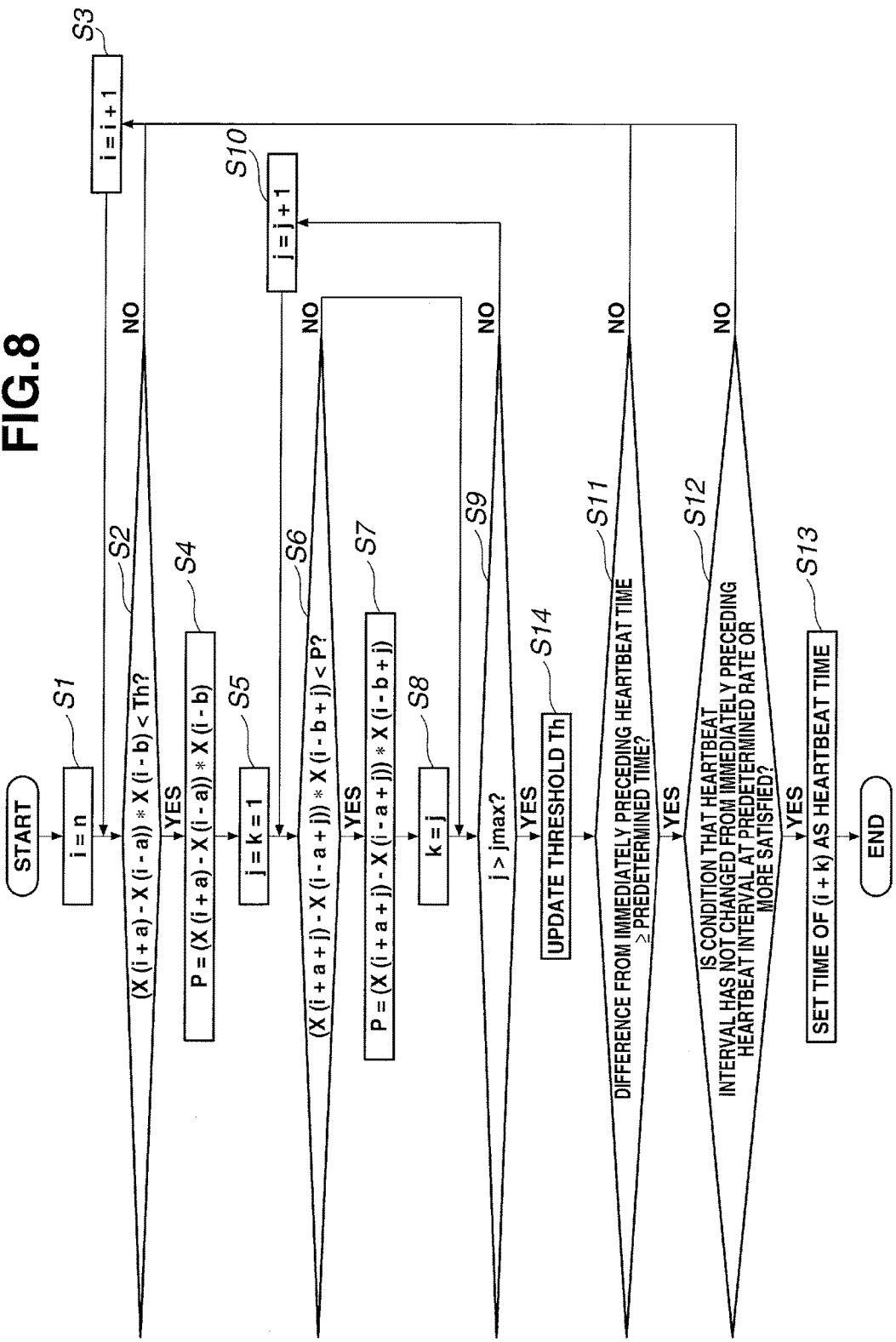
FIG. 8 is a flowchart for explaining another operation of the peak detection unit of the heartbeat detection device according to the embodiment of the present invention.
Figure 9:
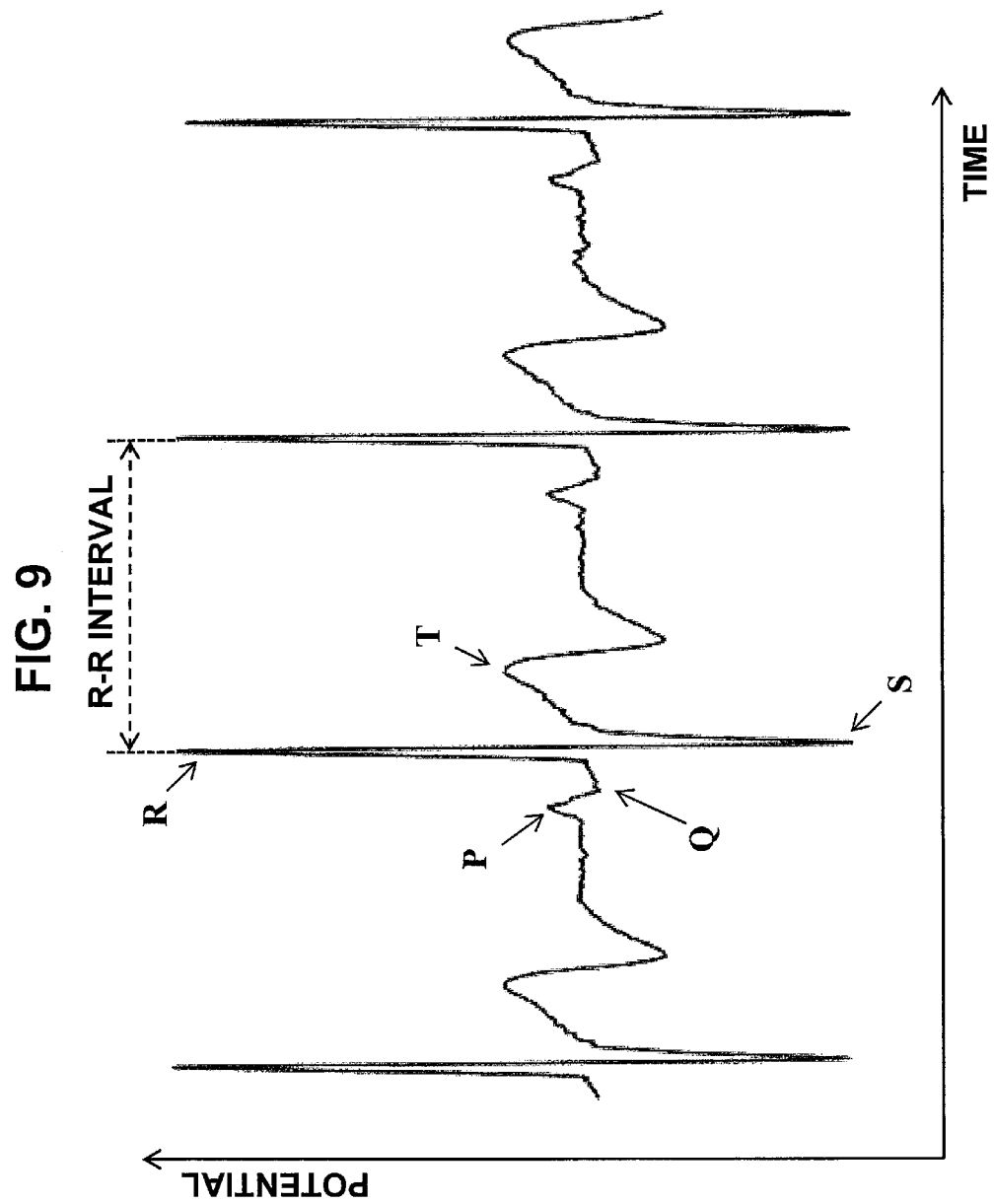
FIG. 9 is a graph showing an example of an electrocardiographic waveform.

Note that the threshold Th may be periodically updated based on the average of the peak values P obtained so far or the like. FIG. 8 shows a flowchart in this case. If YES is determined in step S9, the peak detection unit 5 updates, as the newest threshold Th, a value obtained by multiplying the mean value of the peak values P detected after the start of measurement by a predetermined coefficient r (step S14 of FIG. 8). When the mth heartbeat is to be detected, the (m−1) peak values P have already been detected, and then the peak value P is newly detected. As a result, the m peak values P in total are obtained. Thus, the mean value of the m peak values P is multiplied by the coefficient r. Note that the peak value when NO is determined in step S11 or S12 is not used to calculate the threshold Th.

In the ECG waveform, the amplitude or the degree of change of each component is variable depending on an individual difference or the manner in which electrodes are attached. By setting, based on the average of the peak values P obtained so far, the threshold Th for detecting the peak of the product, it is possible to reduce the influence of a waveform variance caused by an individual difference or the like. Processes other than step S14 in FIG. 8 are as described with reference to FIG. 7.

It is possible to obtain a significant effect by applying the heartbeat detection method according to this embodiment to the ECG waveform of the ECG lead in which a large R wave and a deep S wave are obtained, for example, the ECG waveform of one of the V3 to V5 leads. It is especially preferable to apply the method to the ECG waveform of the CC5 lead or similar lead which is often used to obtain the ECG waveform in daily life.

In the heartbeat detection method according to this embodiment, it is possible to obtain a data sequence of correct heartbeat times, and obtain the highly reliable index of a heartbeat fluctuation based on the data sequence.

Note that this embodiment has explained a case in which a heartbeat is detected using the first derivative value of sampling data. However, the second derivative value may be used, as described above. In this case, the difference value calculation unit 3 calculates the second derivative value of the sampling data X(i) for each sampling time (step S100 of FIG. 6). When the first derivative value of the sampling data X(i) is given by DF(i)=(X(i+a)−X(i−a)), the second derivative value of the sampling data X(i) is given by (DF(i+a)−DF(i−a)).

Consequently, the multiplication unit 4 calculates, for each sampling time, the product (DF(i+a)−DF(i−a))×X(i) of the second derivative value (DF(i+a)−DF(i−a)) of the sampling data X(i) and the sampling data X(i) or the product (DF(i+a)−DF(i−a))×X(i−b) of the second derivative value (DF(i+a)−DF(i−a)) and the sampling data X(i−b) at time the predetermined time t before the sampling data X(i) (step S101 of FIG. 6).

In the description of FIGS. 7 and 8, the product (X(i+a)−X(i−a))×X(i−b) is replaced by (DF(i+a)−DF(i−a))×X(i) or (DF(i+a)−DF(i−a))×X(i−b), and the product (X(i+a+j)−X(i−a+j))×X(i−b+j) is replaced by (DF(i+a+j)−DF(i−a+j))×X(i+j) or (DF(i+a+j)−DF(i−a+j))×X(i−b+j). Thus, it is possible to detect a heartbeat using the second derivative value of the sampling data.

The storage unit 2, difference value calculation unit 3, multiplication unit 4, peak detection unit 5, and heartbeat time determination unit 6 described in this embodiment can be implemented by a computer including a CPU (Central Processing Unit), storage device, and interface and a program that controls these hardware resources. The CPU executes the processing described in this embodiment in accordance with the program stored in the storage device.

INDUSTRIAL APPLICABILITY

The present invention is applicable to a technique of detecting heartbeats of a living body. Explanation of the Reference Numerals and Signs 1 . . . electrocardiograph, 2 . . . storage unit, 3 . . . difference value calculation unit, 4 . . . multiplication unit, 5 . . . peak detection unit, 6 . . . heartbeat time determination unit

The invention claimed is:
1. A heartbeat detection method that is performed by a computer, including a central processor unit, a storage device and an interface, under control of a computer program installed thereon, comprising:

a calculation step of calculating, from a sampling data sequence including sampling data values obtained by sampling an electrocardiographic waveform of a living body at sampling time points, one of an amount of change and a degree of change in the sampling data values of the sampling data sequence for each of the sampling time points;

a multiplication step of calculating, for each of the sampling time points, a product value by multiplying one of an amount of change and a degree of change in the sampling data values of the sampling data sequence at a sampling time point K by one of a sampling data value at the sampling time point K and a sampling data value at a sampling time point a predetermined time period t before the time K;

a peak detection step of detecting a peak of a sequence of the product values calculated for the sampling time points; and a heartbeat time point determination step of setting a sampling time point of the peak of the sequence of the product values as a heartbeat time point;

wherein the peak detection step is performed according to an order of the sampling time points;

the heartbeat time point determination step is performed as a peak of the sequence of the product values is detected, the multiplication step includes calculating a product value for each of the sampling time points by multiplying a first derivative value of the sampling data sequence at the sampling time point K by the sampling data value at the sampling time point the predetermined time period t before the sampling time point K, and the predetermined time period t satisfies 10 ms≤t≤12 ms, said multiplying for smoothing fluctuation components of noise caused by movement of said living body and said setting the sampling time point of the peak of the sequence of the product values as a heartbeat time enables accurate detection of said heartbeats independent of movement of said living body.

2. The heartbeat detection method according to claim 1, wherein the peak detection step includes detecting a sampling time point at which the product value is smaller than a threshold and the sequence of the product values makes a peak.

3. The heartbeat detection method according to claim 2, wherein the peak detection step includes a step of updating the threshold based on an average of peaks of the sequence of the product values detected.

4. The heartbeat detection method according to claim 1, wherein the peak detection step is performed according to an order of the sampling time points; and the heartbeat time point determination step is performed as a peak of the sequence of the product values is detected, and further includes determining whether a difference between a sampling time point of the peak of the sequence of the product values and an immediately preceding heartbeat time point is not shorter than a predetermined time period, and not setting the sampling time point of the peak of the sequence of the product values as a heartbeat time if the difference from the immediately preceding heartbeat time point is shorter than the predetermined time period.

5. The heartbeat detection method according to claim 1, wherein the peak detection step is performed according to an order of the sampling time points; and the heartbeat time point determination step is performed as a peak of the sequence of the product values is detected, and further includes determining whether a heartbeat interval when the sampling time point of the peak of the sequence of the product values is considered as a heartbeat time point has not increased from an immediately preceding heartbeat interval at a rate not lower than a predetermined rate, and not setting the sampling time point of the peak of the sequence of the product values as a heartbeat time if the heartbeat interval has increased at the rate not lower than the predetermined rate.

6. The heartbeat detection method according to claim 1, wherein the amount of change in the sampling data values of the sampling data sequence is a first derivative value of sampling data sequence at each of the sampling time points.

7. The heartbeat detection method according to claim 1, wherein a value indicating the degree of change in the sampling data values of the sampling data sequence is a second derivative value of sampling data, and the predetermined time period t satisfies 0 ms<t≤1 ms.

8. A heartbeat detection device comprising:

a computer, including a central process unit, a storage device and an interface, and a computer program installed thereon, the computer configured to, under control of the computer program, implement:

a calculation unit configured to calculate, from a sampling data sequence including sampling data values obtained by sampling an electrocardiographic waveform of a living body at sampling time points and stored in the storage device, one of an amount of change and a degree of change in the sampling data values of the sampling data sequence for each of the sampling time points;

a multiplication unit configured to calculate, for each of the sampling time points, a product value for each of the sampling time points by multiplying a first derivative value of the sampling data sequence at the sampling time point K by the sampling data value at the sampling time point the predetermined time period t before the sampling time point K, and the predetermined time period t satisfies 10 ms≤t≤12 ms;

said multiplying for smoothing fluctuation components of noise caused by movement of said living body and said setting the sampling time point of the peak of the sequence of the product values as a heartbeat time enables accurate detection of said heartbeats independent of movement of said living body;

a peak detection unit configured to detect a peak of a sequence of the product values calculated for the sampling time points; and a heartbeat time point determination unit configured to set a sampling time point of the peak of the sequence of the product values as a heartbeat time point.

9. A heartbeat detection method that is performed by a computer, including a central process unit, a storage device and an interface, under control of a computer program installed thereon, comprising:

a calculation step of calculating, from a sampling data sequence including sampling data values obtained by sampling an electrocardiographic waveform of a living body at sampling time points, one of an amount of change and a degree of change in the sampling data values of the sampling data sequence for each of the sampling time points;
a multiplication step of calculating, for each of the sampling time points, a product value by multiplying one of an amount of change and a degree of change in the sampling data values of the sampling data sequence at a sampling time point K by one of a sampling data value at the sampling time point K and a sampling data value at a sampling time point a predetermined time period t before the sampling time point K;
a peak detection step of detecting a peak of a sequence of the product values calculated for the sampling time points; and
a heartbeat time point determination step of setting a sampling time point of the peak of the sequence of the product values as a heartbeat time point;
wherein
the peak detection step is performed according to an order of the sampling time points;
the heartbeat time point determination step is performed as a peak of the sequence of the product values is detected,
the multiplication step includes calculating a product value for each of the sampling time points by multiplying a second derivative value of the sampling data sequence at the sampling time point K by one of the sampling data values at the sampling time point K and the sampling data value at the time point the predetermined time period t before the sampling time point K; and
said multiplying for smoothing fluctuation components of noise caused by movement of said living body and said setting the sampling time point of the peak of the sequence of the product values as a heartbeat time enables accurate detection of said heartbeats independent of movement of said living body.

10. A heartbeat detection device comprising:
a computer, including a central process unit, a storage device and an interface, and a computer program installed thereon, the computer configured to, under control of the computer program, implement:
a calculation unit configured to calculate, from a sampling data sequence including sampling data values obtained by sampling an electrocardiographic waveform of a living body at sampling time points and stored in the storage device, one of an amount of change and a degree of change in the sampling data values of the sampling data sequence for each of the sampling time points;
a multiplication unit configured to calculate, for each of the sampling time points, a product value for each of the sampling time points by multiplying a second derivative value of the sampling data sequence at the sampling time point K by one of the sampling data values at the sampling time point K and the sampling data value at the time point the predetermined time period t before the sampling time point K;
a peak detection unit configured to detect a peak of a sequence of the product values calculated for the sampling time points; and
a heartbeat time point determination unit configured to set a sampling time point of the peak of the sequence of the product values as a heartbeat time point; and
said multiplying for smoothing fluctuation components of noise caused by movement of said living body and said setting the sampling time point of the peak of the sequence of the product values as a heartbeat time enables accurate detection of said heartbeats independent of movement of said living body.

* * * * *